United States Patent
Irimia et al.

(10) Patent No.: US 10,168,271 B2
(45) Date of Patent: Jan. 1, 2019

(54) MICROPARTICLES HAVING REFERENCE MARKERS ARRANGED IN DIFFERENT CONCENTRATIONS

(71) Applicant: The General Hospital Corporation, Boston, MA (US)

(72) Inventors: Daniel Irimia, Charlestown, MA (US); Ki Wan Bong, Seoul (KR)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/033,272

(22) PCT Filed: Nov. 3, 2014

(86) PCT No.: PCT/US2014/063730
§ 371 (c)(1),
(2) Date: Apr. 29, 2016

(87) PCT Pub. No.: WO2015/066635
PCT Pub. Date: May 7, 2015

(65) Prior Publication Data
US 2016/0282255 A1    Sep. 29, 2016

Related U.S. Application Data
(60) Provisional application No. 61/898,543, filed on Nov. 1, 2013.

(51) Int. Cl.
| | | |
|---|---|---|
| *G01N 15/14* | (2006.01) | |
| *G01N 33/543* | (2006.01) | |
| *B01L 3/00* | (2006.01) | |
| *G01N 33/569* | (2006.01) | |
| *G01N 33/574* | (2006.01) | |
| *G01N 15/10* | (2006.01) | |

(52) U.S. Cl.
CPC .... *G01N 15/1459* (2013.01); *B01L 3/502761* (2013.01); *G01N 15/1429* (2013.01); *G01N 15/1463* (2013.01); *G01N 15/1484* (2013.01); *G01N 33/54326* (2013.01); *G01N 33/569* (2013.01); *G01N 33/56961* (2013.01); *G01N 33/56966* (2013.01); *G01N 33/56972* (2013.01); *G01N 33/574* (2013.01); *G01N 2015/1006* (2013.01); *G01N 2015/149* (2013.01); *G01N 2015/1488* (2013.01); *G01N 2015/1497* (2013.01)

(58) Field of Classification Search
CPC .............................................. G01N 33/54326
See application file for complete search history.

(56) References Cited

U.S. PATENT DOCUMENTS
| | | |
|---|---|---|
| 7,709,544 B2 | 5/2010 | Doyle et al. |
| 8,807,879 B2 | 8/2014 | Toner et al. |
| 2007/0092958 A1 | 4/2007 | Syed et al. |
| 2010/0120077 A1 | 5/2010 | Daridon |
| 2012/0028342 A1 | 2/2012 | Ismagilov et al. |
| 2012/0065092 A1 | 3/2012 | Wai et al. |
| 2013/0210653 A1 | 8/2013 | Pregibon et al. |

OTHER PUBLICATIONS

Wang et al. Biomaterials, 2011, 32:4903-4913.*
Patel et al. NANO Letters, 2007, 7(7):2122-2128.*
Salata, J of Nanobiotechnology, 2004, 1-6.*
DiVietro et al. The J of Immunology, 2001, 167:4017-4025.*
Cai et al. ACS Applied Materials & Interfaces, 2010, 2(4):1038-1047.*
"Electric Field," Wikipedia [online], [retrieved Feb. 25, 2015] (Retrieved from the Internet) URL<http://en.wikipedia.org/wiki/Electric_field>, 6 pages.
de Calignon et al., "Propagation of tau pathology in a model of early Alzheimer's disease," Neuron, 73(4):685-697, Feb. 2012.
Desai et al., "Mitochondrial localization and the persistent migration of epithelial cancer cells," Biophys J, 104(9):2077-2088, May 2013.
El-Haibi et al., "Critical role for lysyl oxidase in mesenchymal stem cell-driven breast cancer malignancy," Proc Natl Acad Sci USA, 109(43):17460-17465, Oct. 2012.
Hamza et al., "Retrotaxis of Human Neutrophils during Mechanical Confinement inside Microfluidic Channels," Integrative Biology (Cambridge), 6(2):175-183, Feb. 2014.
Hoang et al., "Measuring neutrophil speed and directionality during chemotaxis, directly from a droplet of whole blood," Technology, 1(1):49-57, Oct. 2013.
International Preliminary Report on Patentability in International Application No. PCT/US2014/063730, dated May 12, 2016, 9 pages.
International Search Report and Written Opinion in International Application No. PCT/US2014/063730, dated Mar. 13, 2015, 12 pages.
Jones et al., "Microfluidic chambers for monitoring leukocyte trafficking and humanized nano-proresolving medicines interactions," Proc Natl Acad Sci USA, 109(50):20560-20565, Dec. 2012.
Kolaczkowska et al., "Neutrophil recruitment and function in health and inflammation," Nat Rev Immunol, 13(3):159-175, Mar. 2013.
Mathias et al., "Neutrophil motility in vivo using zebrafish," Methods Mol Biol, 571:151-166, 2009.
Renshaw et al., "A transgenic zebrafish model of neutrophilic inflammation," Blood, 108(13):3976-3978, Dec. 2006.

(Continued)

*Primary Examiner* — Bin Shen
(74) *Attorney, Agent, or Firm* — Fish & Richardson P.C.

(57) ABSTRACT

Methods for sorting cells include: arranging microparticles into an array on a substrate in a microfluidic device, in which the microparticles each include multiple reference markers; introducing multiple cells to the array of microparticles under conditions that enable at least some of the cells to adhere to the microparticles; removing the microparticles, to which the cells are adhered, from the substrate; transferring the microparticles, to which the cells are adhered, to a detection region; and detecting, for each of two or more microparticles that pass through the detection region, a microparticle feature; and sorting the two or more microparticles based on the detected features, in which the detected features are related to a phenotype of the cells.

17 Claims, 11 Drawing Sheets

(56) References Cited

OTHER PUBLICATIONS

Scherber et al., "Epithelial cell guidance by self-generated EGF gradients," Integr Biol (Camb), 4(3):259-269, Mar. 2012.
Smolen et al., "A genome-wide RNAi screen identifies multiple RSK-dependent regulators of cell migration," Genes Dev, 24(23):2654-2665, Dec. 2010.
Stoothoff et al., "Differential effect of three-repeat and four-repeat tau on mitochondrial axonal transport," J Neurochem, 111(2):417-427, Oct. 2009.
Wang et al., "Engineering chemoattractant gradients using chemokine-releasing polysaccharide microspheres," Biomaterials 32(21):4903-4913, 2011.
Wolfer et al., "MYC regulation of a "poor-prognosis" metastatic cancer cell state," Proc Natl Acad Sci USA, 107(8):3698-3703, Feb. 2010.
Yan et al., "Stochastic variations of migration speed between cells in clonal populations," Technology (Singap World Sci), 2(3):185-188, Sep. 2014.

\* cited by examiner

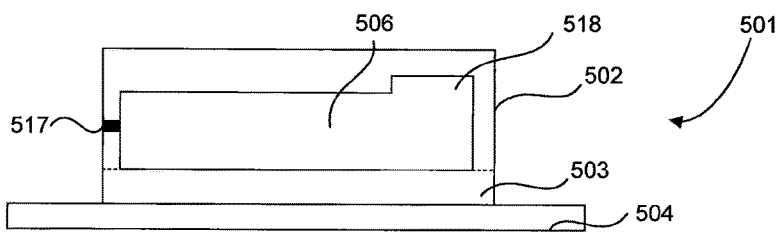
FIG. 5A
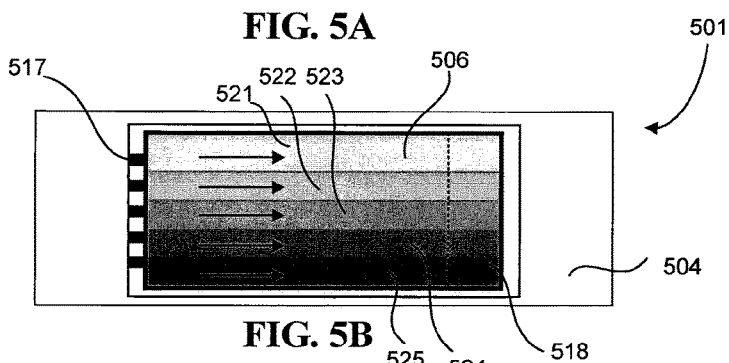
FIG. 5B
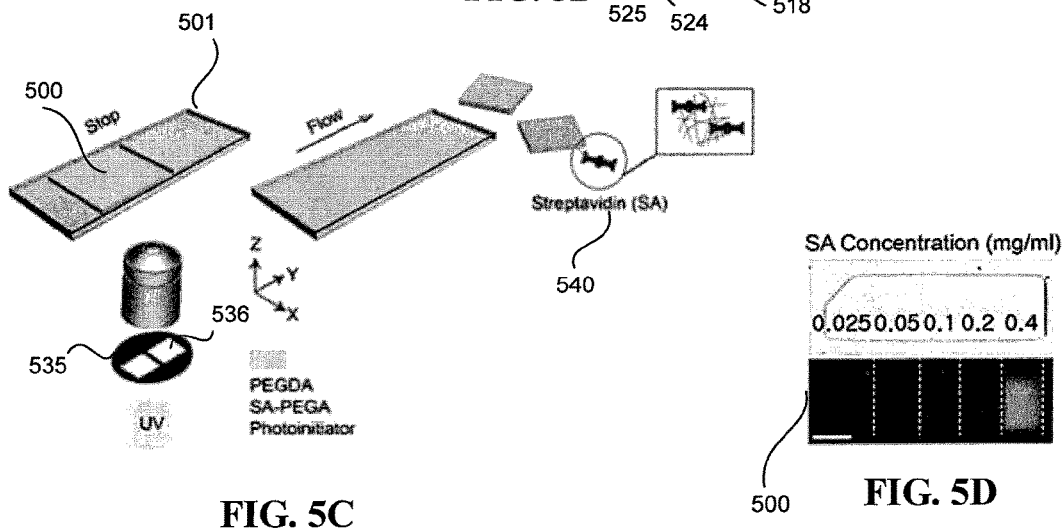
FIG. 5C
FIG. 5D

US 10,168,271 B2

MICROPARTICLES HAVING REFERENCE MARKERS ARRANGED IN DIFFERENT CONCENTRATIONS

CROSS-REFERENCE TO RELATED APPLICATIONS

This application is a U.S. national stage application under 35 USC § 371 of International Application No. PCT/US2014/063730, filed on Nov. 3, 2014, which claims priority to U.S. Provisional Patent Application No. 61/898,543, filed on Nov. 1, 2013, the entire contents of each of which is incorporated herein by reference.

TECHNICAL FIELD

This disclosure relates to cell sorting.

BACKGROUND

Cell sorting is one of the vital technologies for biomedical research. The goal of sorting is generally to isolate homogenous populations of cells that share specific phenotypes from heterogeneous samples. Most often, cell sorting is performed based not on the target phenotype, but rather on the intensity of one or more fluorescent markers expressed selectively by these cells. Typically, these markers have to be known a priori and represent a fundamental limitation for the current technologies, because (1) they cannot be applied to phenotypes for which fluorescent biomarkers do not exist yet, and (2) they are reductionist and incompatible with complex phenotypes. Although high-content, high-throughput imaging platforms can analyze many complex phenotypes in detail, they lack the ability to sort the cells of interest. Even when integrated with "cell picking" technologies, the throughput of sorting is very small and impractical for any comprehensive downstream analysis.

SUMMARY

The present disclosure is related to sorting cells based on a phenotype by using multifunctional particles tailored with specific functionalities. In particular, the present disclosure covers systems and methods in which multiple multifunctional particles are arranged into an ordered array on a substrate surface. The ordered array of particles then is introduced to a fluid sample containing groups of cells, which attach or adhere to the particles. The array of particles containing the cells then is released from the substrate surface and the particles are transferred to a detection region, in which the phenotypes of the cells are detected. The particles then are sorted based on the detected phenotypes.

In general, in one aspect, the subject matter of the present disclosure can be embodied in tubular multifunctional microparticles, each of which incorporates a chemokine concentration gradient. These multifunctional microparticles are fabricated to include magnetic components so that the particles can be rapidly and simultaneously ordered into the same orientation. A cell interacting with the multifunctional microparticle travels at a certain rate through the microparticle in response to the chemokine concentration gradient. After being loaded with cells, the multifunctional microparticles are sent through a particle focusing device that allows a continuous interrogation of each particle. Each interrogation identifies the microparticle and determines the distance the cell has traveled within the microparticle. In this embodiment, the tubular multifunctional microparticles facilitate rapid detection of cells with a particular phenotype for cell motility (e.g. fast or slow).

In general, in one aspect, the subject matter of the present disclosure may be embodied in methods of sorting cells, in which the methods include: arranging multiple microparticles into an array on a substrate in a microfluidic device, in which the microparticles each includes multiple reference markers; introducing multiple cells to the array of microparticles under conditions that enable at least some of the cells to adhere to the microparticles; removing the microparticles, to which the cells are adhered, from the substrate; transferring the microparticles, to which the cells are adhered, to a detection region; and detecting, for each of two or more microparticles that pass through the detection region, a microparticle feature; and sorting the two or more microparticles based on the detected features, in which the detected features are related to a phenotype of the cells.

Implementations of the methods may have one or more of the following features. For example, in some implementations, each microparticle includes a porous material. The porous material can include polyethylene glycol.

In some implementations, each microparticle includes a tubular shape having an opening that extends through the microparticle.

In some implementations, the reference markers include fluorescent markers.

In some implementations, for each microparticle, the reference markers are arranged in two or more regions on the microparticle. Each of the two or more regions may have a different concentration of the reference markers.

In some implementations, for each microparticle, the reference markers are embedded within the microparticle.

In some implementations, for each microparticle, the reference markers are attached to a surface of the microparticle. In some implementations, the reference markers include a chemoattractant, a fluorescent marker, a magnetic marker, a geometric marker, and/or a mechanical marker.

In some implementations, reference markers include multiple chemoattractants, in which, for each microparticle, the chemoattractants are arranged to establish a concentration gradient over a region of the microparticle, and in which the methods further include allowing the cell that is adhered to the microparticle to propagate within or along the microparticle in response to the concentration gradient.

In some implementations, each microparticle includes multiple magnetic particles, in which arranging the microparticles includes applying a magnetic field to the microparticles such that the microparticles align with the magnetic field on the substrate. Removing the microparticles may include removing the magnetic field.

In some implementations, a surface of the substrate includes multiple wells, in which each well includes a cross-section that matches a cross-section of one of the microparticles, and in which arranging the microparticles includes positioning the microparticles in the wells.

In some implementations, introducing the multiple cells to the array of microparticles includes creating a pressure-differential that causes the cells to propagate in a direction of the array of microparticles. The substrate may be porous, and creating the pressure-differential may include creating a fluid flow through porous regions of the substrate.

In some implementations, detecting the microparticle feature includes detecting a fluorescent signal from the microparticle, in which the fluorescent signal corresponds to a position of a cell in or on the microparticle. For each of the two or more microparticles, sorting may be based on the position of the cell. The methods may further include determining, for at least one of the sorted microparticles, an amount that a cell has moved within or along the microparticle to which the cell is adhered.

In some implementations, the cells include multiple neurons, multiple tumor cells, white blood cells, epithelial cells, amoebas, fungi, and/or bacteria.

In some implementations, the methods further include, subsequent to introducing the cells, applying an electrical or chemical stimuli to two or more of the microparticles. In some implementations, the methods further include allowing cells to move or grow in response to the electrical or chemical stimuli. The chemical stimuli may be a chemokine concentration gradient, in which the reference markers include chemoattractants arranged to establish the chemokine concentration gradient. The electrical stimuli may be an applied magnetic field.

In some implementations, the cells include neurons, in which the methods further include subsequent to introducing the cells, applying an electrical stimulus to the neurons that are adhered to the microparticles and allowing axons to grow from the neurons in response to the electrical stimulus. Detecting the microparticle feature may include detecting a fluorescent signal that corresponds to an extent of axon growth within or along the microparticle. The methods may further include sorting the two or more microparticles based on the how far each axon has grown.

In some implementations, the microparticle further includes a tag that uniquely identifies the microparticle. The tag may be a bar code.

In general, in another aspect, the subject matter of the present disclosure can be embodied in a microparticle that includes multiple reference markers embedded within or attached to a surface of the microparticle, in which the reference markers are arranged in two or more regions, each region having a different overall concentration of the reference markers, and in which the microparticle is tubular.

In some implementations, the reference markers include chemoattractants, in which the reference markers arranged in the two or more regions establish a chemokine concentration gradient within or along the microparticle.

In some implementations, the reference markers include fluorescent markers.

In some implementations, the microparticle further includes a tag that uniquely identifies the microparticle. The tag may include a bar-code.

In some implementations, the microparticle is composed of polyethylene glycol.

In some implementations, the microparticle is porous. An average diameter of the pores in the microparticle may range between about 10 nm to 100 nm.

In some implementations, the microparticle further includes magnetic particles.

For the purposes of this disclosure, a microparticle is understood to include a particle having at least one cross-sectional dimension in the range of 50 nm to about 1000 µm.

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

BRIEF DESCRIPTION OF THE DRAWINGS

FIG. 5A is a side view schematic of a microfluidic device used to fabricate multifunctional particles using stop-flow lithography.
FIG. 5B is a top view schematic of a microfluidic device used to fabricate multifunctional particles using stop-flow lithography.
FIG. 5C is a schematic illustrating a stop-flow lithography process.
FIG. 5D is a schematic depicting the different streptavidin concentrations along a microparticle.

DETAILED DESCRIPTION

The multifunctional particles and the system to sort these particles described herein enable the separation of cells based on their functional abilities with respect to phenotypes such as cell migration, motility, and cellular tightness. Multifunctional particles with distinct layers having varying compounds can be fabricated, giving each layer a differentiated function. For example, multifunctional particles having an increasing amount of streptavidin in each layer can be manufactured using the processes described in this disclosure.

Figure 1:
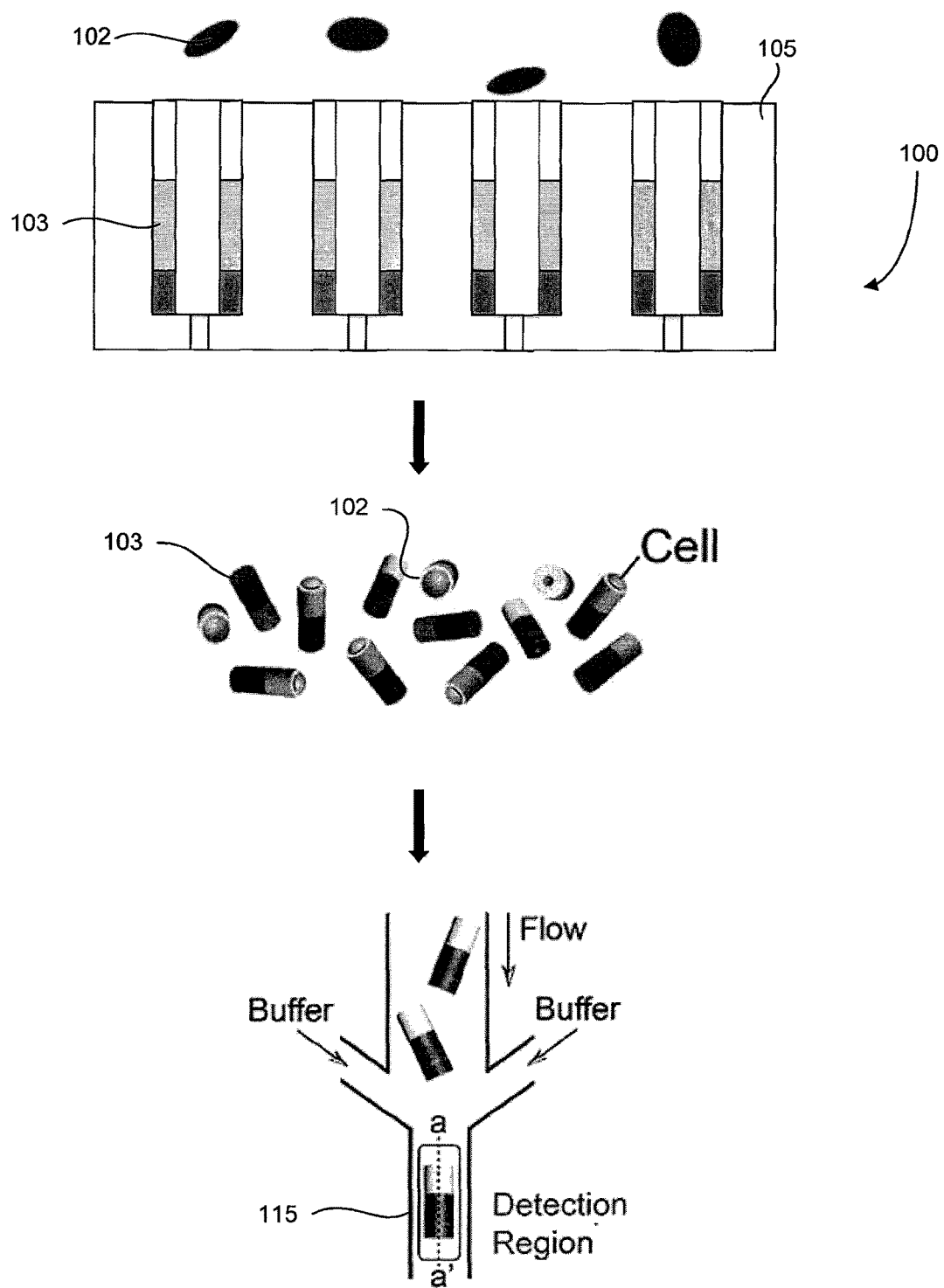
FIG. 1 is a schematic that illustrates a cell sorting system.

FIG. 1 illustrates a cell sorting system 100 that can be used to sort cells 102 based on a cell phenotype, in which the system 100 relies on the use of multifunctional particles that enable both the long term observations of cells and cell separation. The multifunctional particles are micro-scale particles that integrate mechanical, biochemical, fluorescent, magnetic, and/or electrical features to build multifunctional platforms for culturing, stimulating, imaging, and sorting live cells. As will be described in more detail below, the system 100 includes a particle orienting device 105 and a particle focusing and detection region 115. In device 105, multiple multifunctional particles 103 are arranged and oriented in an array. For example, in some implementations, the microparticles 103 may include magnetic material (e.g., magnetic nano-particles), such that the application of a magnetic field causes the particles 103 to orient themselves along identical directions on the particle orienting device 105. Once the particles 103 are positioned on the particle orienting device 105, cells 102 then are introduced and adhere to the particles 103 (e.g., by entering openings in the multifunctional particles 103). The array of microparticles 103 may be temporarily fixed to the particle orienting device 105. That is, in some implementations, the force applied to microparticles to keep them in position may be removed or deactivated so that the microparticles can be released from the particle orienting device 105. Accordingly, after the cells 102 adhere to the particles 103, the particles 103 are released from the substrate and transferred to the particle focusing and detection region 115. The particular cell phenotype for the trait of interest is identified in the particle focusing and detection region 115, after which the particles, and thus cells, can be sorted based on the detected phenotype.

Multifunctional Particle Structure

Figure 2:
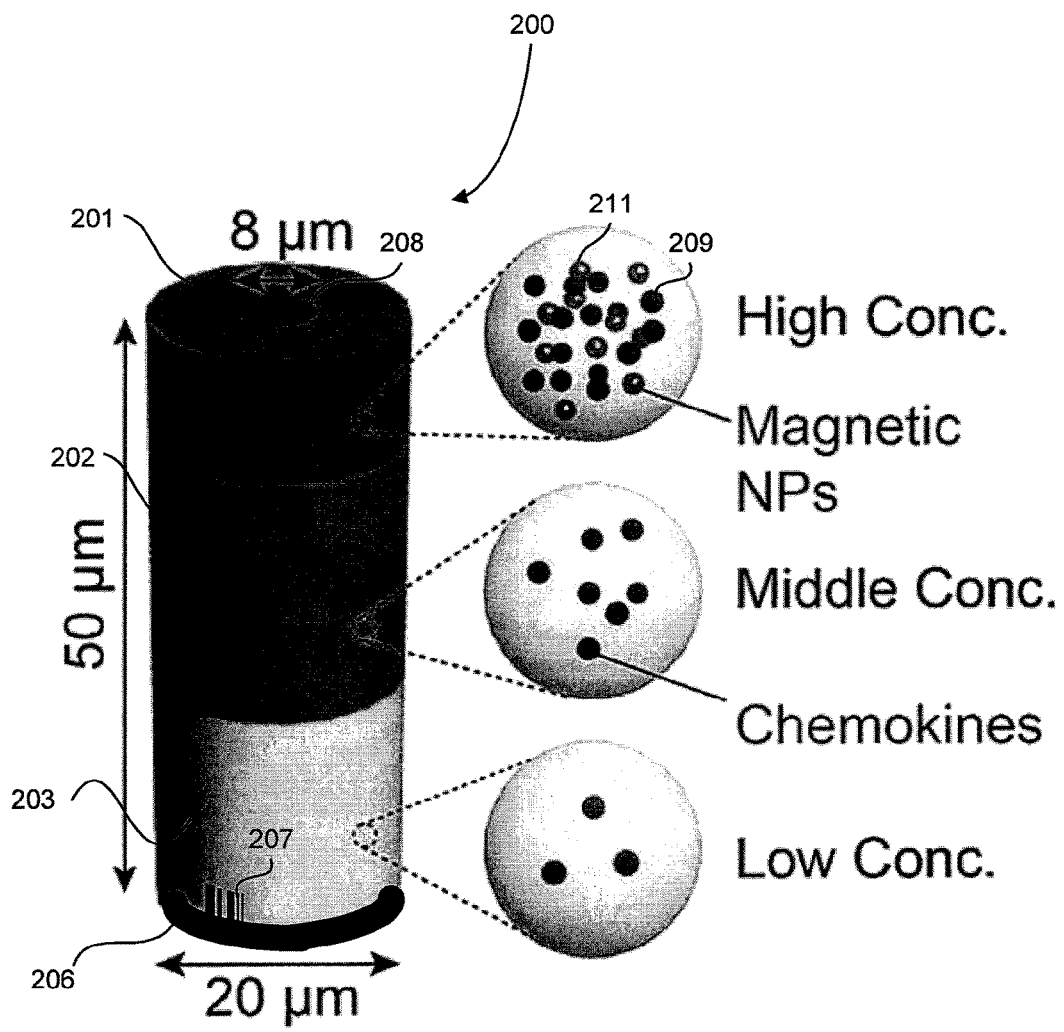
FIG. 2 is a schematic of an example of a multifunctional particle.

FIG. 2 is a schematic that shows an example of a multifunctional particle 200 that can be deposited into the substrate described above in FIG. 1. The multifunctional particle 200 may include multiple layers 201-203, one or more reference markers 206, and an optional tag 207 for unique identification and tracking of the microparticle 200. The multifunctional particle 200 further includes a through-channel 208. In some implementations, one or more of the layers 201-203 may also contain other components, such as streptavidin 209 so as to facilitate the binding of biotinylated molecules to the surface of the multifunctional particles. In this example, layers 201-203 have an increasing concentration of streptavidin in preparation for forming a biotinylated molecule concentration gradient.

In some implementations, the multifunctional particle 200 also includes multiple orientation components. The orientation components may be used to orient the multifunctional particle 200 along a desired direction or to a desired position. For example, the microparticle 200 in FIG. 2 includes magnetic nanoparticles 211 incorporated into layer 203. When a magnetic field is applied to the particle 200, the magnetic components 207 may cause the particle to orient itself along the direction of the magnetic field.

The one or more reference markers 206 can contain fluorescent dye and may be used as a reference for a geometric location on the multifunctional particle 200. The tag 207 serves as a unique identifier for a specific multifunctional particle 200. In some implementations, the tag 207 can provide a fluorescent signal to an individual multifunctional particle. In other implementations, a multifunctional particle 200 can feature unique geometry, such as a pattern of etchings, which differentiates it from other multifunctional particles. Extracellular matrix materials bind to the surface of the multifunctional particles 200. The extracellular matrix materials are biotinylated, facilitating a bond between the materials and the streptavidin in layers 201-203. Due to differing concentrations of streptavidin mixed in the layers, the extracellular matrix materials vary in density depending on the layer as well. The extracellular matrix materials can include one or more different materials. For example, in some implementations, the extracellular matrix materials include fluorescent proteins to serve as a surface marker on the multifunctional particles 200. The extracellular materials can also include biotinylated collagen, which encourages adhesion to certain cells. In other implementations, the materials can include biotinylated chemoattractants, which can be used to induce motility of cells passing through the multifunctional particles. The chemoattractants may have different densities in the different layers 201-203, such that a chemoattractant concentration gradient is established across the particle 200. Thus, when cells that are responsive to chemoattractant gradients (e.g., neutrophils) are loaded into or on the particle 200, the cells may move in response to the established gradient.

The microparticle 200 is shown as having a tubular shape, where an opening 208 extends from one face of the tube through the particle 200 to another opposite face of the tube. The opening 208 can be used to receive and capture cells to be sorted. The openings 208 can have an average diameter ranging in size from about 1 to about 50 μm. While FIG. 2 shows the multifunctional particle 200 in a tubular shape, the multifunctional particle 200 can take the form of a wide range of 3D shapes. For example, the multifunctional particle 200 can be fabricated to have a cylinder shape, a cube shape, a rectangular prism shape, among other shapes.

The number of layers and the specific combination of layers may vary in alternative implementations. For example, in some implementations, the multifunctional particle may not have the markers and the barcode. The multifunctional particle 200 may have chemical components other than streptavidin, fluorescent dyes, magnetic nanopolymers, and adhesive particles. While the one or more reference markers has been described as comprising a fluorescent dye, in other implementations, the reference markers can include other components or properties. For example, the reference markers may include optical markers (e.g. geometric features such as indentations, protrusions, color, transparency), electrical markers (e.g. dielectric and/or conductance features, metal patterns), magnetic markers (e.g. orientation of one or more magnetic dipoles, permittivity features), and mechanical markers (e.g. microparticle geometry, mass, density, elasticity, deformability, buoyancy, and/or symmetry or asymmetry). The microparticle 200 may be formed from a porous material such as polyethylene glycol (PEG). However, any suitable biocompatible material may be used to form the microparticle 200.

Particle Orienting Device Structure

Figure 3A:
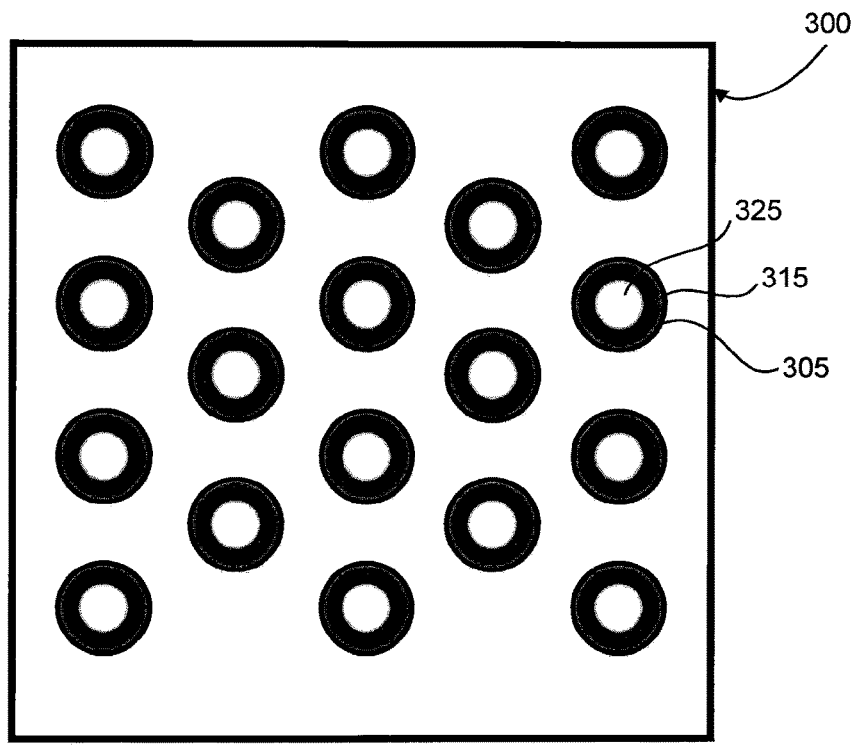
FIG. 3A is a top view schematic of multifunctional particles deposited in an array of microwells on a particle sorting device.
Figure 3B:
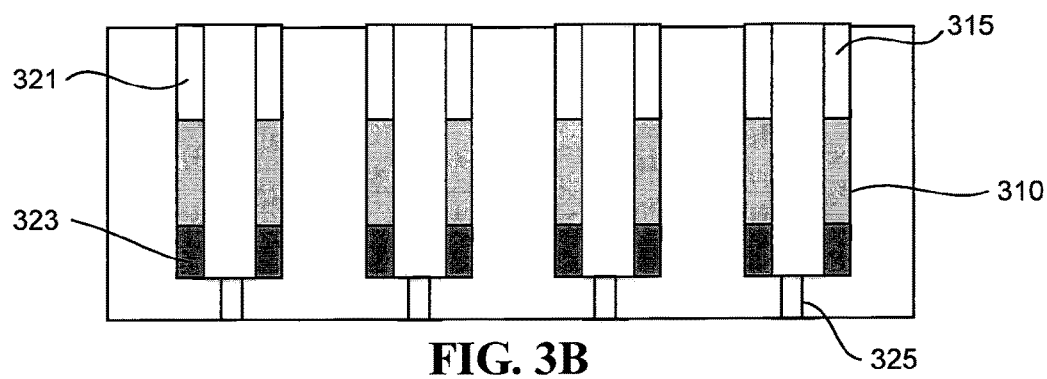
FIG. 3B is a side view schematic of multifunctional particles deposited in an array of microwells on a particle sorting device.

FIG. 3 depicts a particle orienting device 300 that has an array of microwells 305 shaped and sized to accept the multifunctional particles 315 described in FIG. 2. The microwells 305 have a particle channel 310 and a through-hole 325 at the end of the particle channel 310. The shape of the particle channel 310 is fabricated to match the geometry of the multifunctional particles 315 of interest. The throughholes 325 allow a suction device to guide a flow of the multifunction microparticles 315 into the channels. For example, the suction device can generate a pressure drop under the particle channels 310 so as to guide the flow of the multifunctional particles 315, and thus the multifunctional particles 315, into the particle channels 310. As shown, the channels 310 and the multifunctional particles 315 both have circular cross sections of similar dimensions. The multifunctional particles 315 are positioned in the channels 310 such that the longitudinal axes 320 of the microparticles are all parallel and pointing towards the same direction. The bottom surface of the multifunctional particle 315 mates with the bottom of the channel 310. The bottom layer 323 includes magnetic nano-polymers and is oriented towards the bottom of the channel 310.

While FIG. 3 shows that the multifunctional particles 315 as almost fully embedded in the wells 305, in some implementations, the well depth is less than the length of the microparticle, such that only a portion (e.g., half or one-quarter) of the microparticle is positioned in the well. While a suction device has been described to guide the microparticles into the particle orienting device, in alternative embodiments, other methods known in the art to generate a force on the microparticles to guide them into the microwells can be used. For example, a pump above the microparticle orienting device can be used to force a fluid containing the microparticles to flow downward into the wells. In alternative embodiments, the particle orienting device does not orient the multifunctional particles by applying a magnetic field to act on the magnetic nano-particles contained in the microparticles. Instead, the system relies on the structure of the microparticles to orient the microparticles in the microwells in the same direction. For example, the multifunctional particles 315 could have a structure that favors a particular orientation in gravity, e.g. the multifunctional particle could have be asymmetrically weighted such that the heavier side tends to orient itself downward due to gravity. Vacuum suction can then be applied to draw the microparticles into the microwells. In some implementations, the multifunctional particles 315 can have a slightly larger diameter than the channels 310 so as to create a tight friction fit when the microparticles 315 deposit into channels 310 due to the suction force. FIG. 3 depicts the shape of the channels 310 and multifunctional particles 315 as circular, but the cross-section can be of other shapes, such as triangular, rectangular, and hexagonal.

Particle Focusing Device Structure

Figure 4:
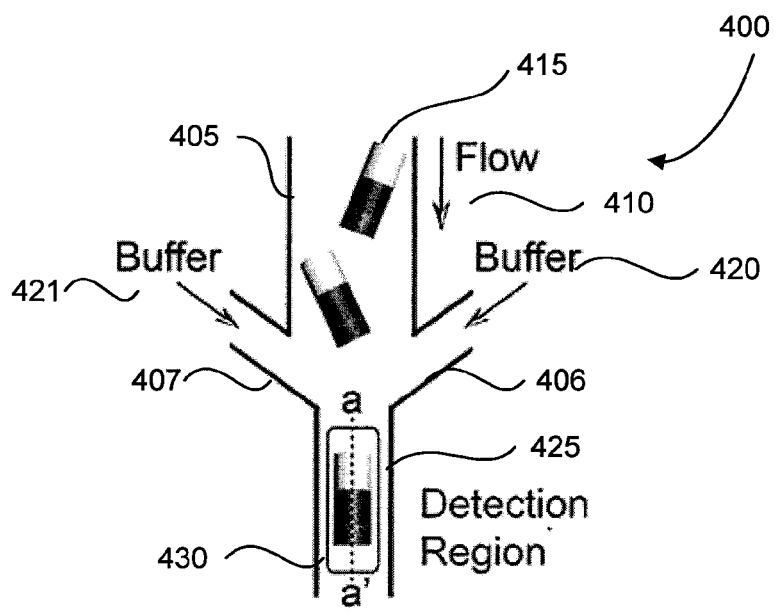
FIG. 4 is a schematic of an example cell sorting device.

Now referring to FIG. 4, a particle focusing device 400 includes a conduit 405 for a flow 410 of multifunctional particles 415 with captured cells and two branching conduits 406-407 for flows of buffer solution 420-421. Flow-focusing techniques are used to align the multifunctional particles 415 as they advect towards a detection channel 425 that contains a detection region 430. In the case as shown in FIG. 4, an example of a flow-focusing technique that can be used involves generating a laminar flow of the three streams of fluid—the two buffer solutions 420-421 and the flow 410 of multifunctional particles 415—as they are brought together. In the detection channel 425 where the solutions join together, the width of each stream 410 and 420-421 is proportional to the flow rate of the streams. The lateral streams of buffer solutions 420-421 could have a higher flow rate than the flow 410. As a result, the flow 410 has a smaller width in the detection channel 425 and enables the focusing of the microparticles 415 present in the flow 410 as they pass through the detection channel 425. In some implementations, a surfactant may be added to the buffer solutions in order to prevent the microparticles from sticking The detection channel 425 is sized and shaped to only allow a single multifunctional particle 415 to pass through at a time. The microparticle 415 is detected and scanned, a process which will be explained in more detail later in this application. For example, for the exemplary microparticle shown in FIG. 2, the detection channel 425 can have a width of 25 μm so only one microparticle can enter the channel.

While flow focusing techniques have been described to direct the microparticles into the detecting channel, in other implementations, inertial focusing techniques can be used to focus the microparticles. Further information on inertial focusing of microparticles may be found, for example, in U.S. Pat. No. 8,807,879, which is incorporated herein by reference in its entirety. While the particle orienting device and particle focusing device have been described as separate devices, it should be understood that they can be part of the same device, or be modules within a system. For example, applying a magnetic field in the direction of the flow could orient the particles with their longer dimension along the flow lines.

Fabrication

FIGS. 5A-D depicts the fabrication of an exemplary multifunctional particle 500 using stop-flow lithography. FIG. 5A shows a top view of a microfluidic device 501 that can serve as a negative mold for the multifunctional particle 500. FIG. 5B shows a side view of the same device 501 with exemplary parallel laminar flows. Referring to FIGS. 5A-B, a microfluidic device 501 has a particle synthesis layer 502 bonded to a substrate layer 503 overlying a glass slide 504. The microfluidic device 501 further contains a particle synthesis chamber 506 defined by the particle synthesis layer 502 and the substrate layer 503. The particle synthesis chamber 506 matches the geometry of the multifunctional particle 500 to be fabricated. The particle synthesis layer 502 can be made from a molding manufacturing process. A particle synthesis layer mold can be made of photoresist and can be fabricated using a soft lithography method. Uncured PDMS is then poured into the mold and cured to form the particle synthesis layer 502. The mold can include features that correspond to the particle synthesis chamber 506 on the microfluidic device 501. The particle synthesis chamber 506 is partially defined by the cavity on the particle synthesis layer 502. In preparation for stop-flow lithography, inlet holes 517 can be punched through into the cavity, and a particle collection reservoir 518 can be cut into the cavity.

The glass slide 504 is coated with uncured PDMS. To ensure uniform coating, any liquid coating method known in the art can be applied, including but not limited to spin coating and spray coating. The uncured PDMS is partially cured to form the substrate layer 503 and partially bond the substrate layer to the glass slide 504. The particle synthesis layer 502 is placed on top of the substrate layer 503 to form the microfluidic device 501 and the particle synthesis chamber 506. The microfluidic device 501 is then cured to bond the particle synthesis layer 502 with the substrate layer 503 at their interface 507.

While photolithography is described to fabricate the mold used to create the particle synthesis layer 502, other methods of creating rigid components can also be implemented, e.g. high-resolution 3D printing and stereolithography. While the mold includes features to generate the particle synthesis chambers 506, the mold should not be understood to require these features. For example, the particle synthesis chambers 506 can be manually cut. While both the particle synthesis layer 502 and the substrate layer 503 are both described to be made of PDMS, one or both of the layers can be of different materials. For example, the particle synthesis layer 502 can be of a different material from the substrate layer 503. As already mentioned, the materials can be of any moldable material compatible with soft microfluidics. While the step of partially curing the substrate layer 503 is described to facilitate the bonding of the substrate layer 503 to the particle synthesis layer 502, other methods of adhering elastomers can be used, including epoxy and glue bonding.

FIG. 5C illustrates the stop-flow lithography process utilized to form the multifunctional particles 500. Five fluid flows of UV-curable polymer solutions are introduced into the microfluidic device 501. The flows are laminar and parallel so that the each layer of a multifunctional particle is substantially distinct from one another. Each parallel flow can contain different compounds and materials so as to confer specific functional characteristics to the microparticles, such as those described in FIG. 2 for the tubular multifunctional particles.

Further information on the fabrication of microstructures using stop flow lithography may be found, for example, in U.S. Pat. No. 7,709,544, which is incorporated herein by reference in its entirety.

Referring to FIG. 5B, in one example, polyethylene glycol (PEG) monomer solutions are mixed with different amounts of a solution of streptavidin-PEG-acrylate to form five precursor solutions 521-525 of increasing concentrations of streptavidin. Solution 521 may also contain magnetic nanoparticles.

Now referring to FIG. 5C-5D, exemplary multifunctional particles 500 are fabricated with one PEG monomer solution and streptavidin-PEG-acrylate solution described above. A microfluidic device 501 is placed on a UV light source 530, e.g. an inverted microscope, and a photomask 535 is placed between the light source 530 and the microfluidic device 501. The photomask 535 includes holes 536 that govern the geometry of the resulting multifunction particles 500. For example, a square hole in the photomask would allow UV light focused in the general shape of a square to pass, and solution in contact with the UV light would cure, while solution unexposed to the light would not.

As a result, a cured square multifunctional particle would form in the solution. Still referring to FIG. 5, precursor solutions 521-525 are introduced into the chamber 506 using a flow control system that generates pulsed operation of repeating "stop" and "flow" steps. During the "stop" step, the flows are exposed to the UV light source 530, polymerizing a stationary array of particles via UV exposure through the photomask 535.

In some implementations, the reference markers (e.g., fluorescent markers) may be included in the polymer solution and are incorporated into the polymerized particles upon exposure. The short duration of UV exposure is sufficient to largely retain streptavidin activity, which will later be used to attach surface molecules to give additional functional characteristics to the microparticles. During the "flow" step, the polymerized multifunctional particles 500 advect within the surrounding un-polymerized precursor solution and are harvested in the particle collection reservoir 518. The chamber 506 and the chemistries of the solutions 521-525 are selected such that stable laminar parallel flows can be achieved. The monomer residence time is sufficiently low to reduce diffusion between the laminar interfaces of the parallel flows of solutions 521-525.

FIG. 5D indicates the different strepatavidin concentration at different regions of the microparticle and the corresponding fluorescence. Referring to FIG. 5D, the multifunctional particles 500 are removed from the particle collection reservoir 518 and are washed in a solution of biotin-labeled extracellular matrix materials. The materials bind to the surface of the multifunctional particles 500 via a streptavidin-biotin bond. The extracellular matrix material used is biotinylated fluorescein isothiocyanate (FITC). Unbound materials 540 are washed away. The density of materials bonded to the surface depends on the precursor solution 521-525 that formed that surface during the stop-flow lithography step discussed above. For example, a layer with a greater concentration of streptavidin 540 will bind a greater density of biotinylated molecules.

In some implementations, components of the multifunctional particles can be either physically entrapped in the polymer structure or be chemically bonded on the surface of the multifunctional particles. For example, a component (e.g. magnetic nano-polymers, fluorescent components) can be mixed into one of the precursor solutions to imbue a functionality or characteristic in a particular layer. Alternatively, the component can be biotinylated such that it bonds to a specific layer of the multifunctional particle via a streptavidin-biotin click chemistry. If multiple layers contain streptavidin, to prevent contamination of other layers, a wash of the biotinylated component can be directed such that it only will flow past a particular layer, e.g. other layers of the multifunctional particle could be masked during the wash step. While five precursor solutions 521-525 of varying concentrations of streptavidin are shown and described in FIG. 5B, any number of solutions of different concentrations of streptavidin and other components may be used. For example, one or more precursor solutions may include fluorescent dye, food coloring, or other chemicals to create a visible demarcation between layers of the multifunctional particles. In particular, the multifunctional particles 500 could be Janus particles, which are particles with distinct surfaces having different properties. An example of such an implementation will be described in more detail. While the streptavidin-biotin bond is described as a means of binding extracellular matrix materials 540 to the surface of the multifunctional particles 500, any pair of conjugates or click-chemistry components known in the art can be implemented to facilitate the deposition of the extracellular matrix materials. While FIGS. 5A-D show the multifunctional particles 500 in a rectangular shape, the multifunctional particles 500 can take the form of a wide range of 3D shapes depending on the photomask used, including triangular prisms, hexagonal prisms, and cylinders. The stop-flow lithography process can also be adapted to allow for additional features, such as holes, in the 3D shapes. For example, a tubular microparticle with a through-channel can be generated using the same stop-flow lithography process. In addition, the size of each layer can vary within a multifunctional particle by varying the size of the flow of solutions.

Figure 6:
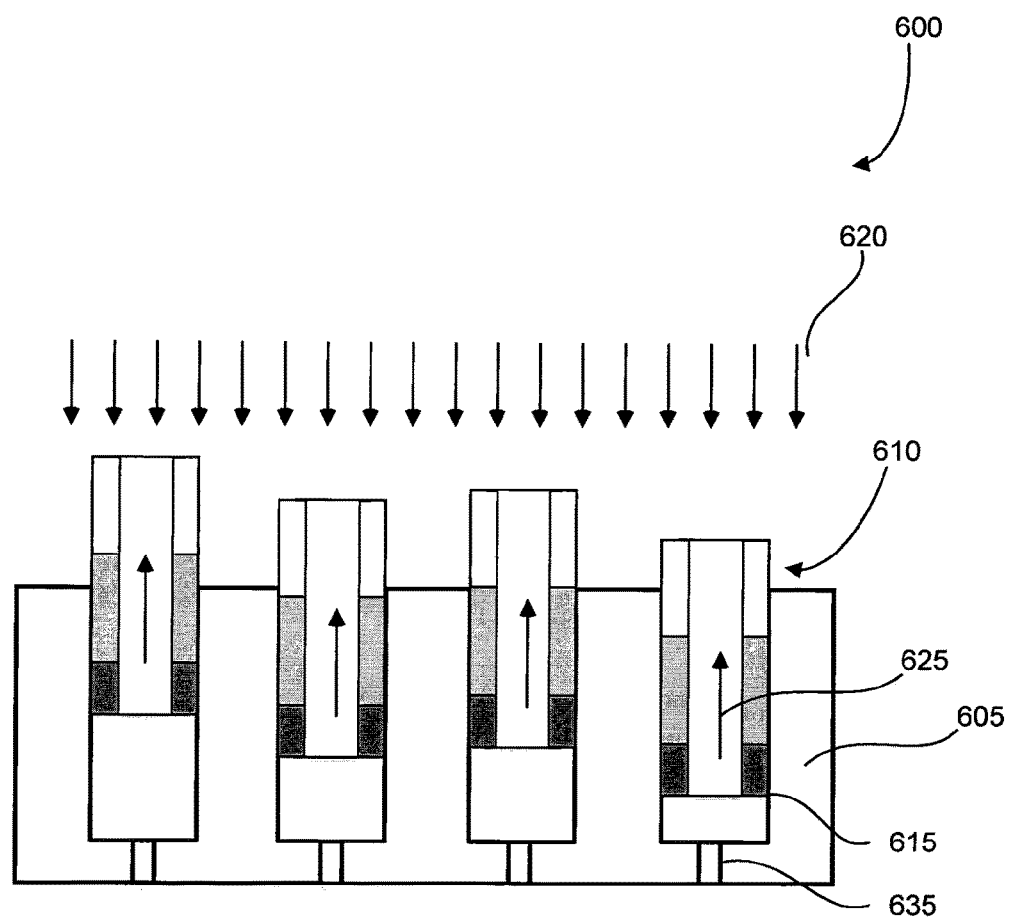
FIG. 6 is a side view schematic of a particle sorting system with multifunctional particles oriented in microwells in the particle sorting system.

Referring to FIG. 6, a particle orienting system 600 includes a particle orienting device 605 and multifunctional particles 610. The particle sorting device 605 can be fabricated using lithography, injection molding, 3D printing, or any method known in the art to form elastomeric or plastic components with well and hole geometries. The multifunctional particles 610, each with a layer containing magnetic nano-polymers 615, are formed using the method described above. An external magnet (not shown) can be activated to generate a uniform magnetic field 620 through the system such that the magnetic nano-polymers 615 in the multifunctional particles 610 respond similarly to the magnetic field. As a result, the longitudinal axes 625 of the multifunctional particles 610 all tend toward the same favored orientation.

Suction is applied at the through-holes 635 of the particle sorting device. The multifunctional particles 610 are deposited into the microwells 640 of the particle orienting device 605 in the same orientation.

While a magnetic field is described as a means to orient the particles in the particle orienting device, other methods could be used to ensure the particles enter the microwells in the same orientation. For example, in some embodiments, the particles could be weighted such that gravity favors a particular orientation as the particles drop into the wells. In other implementations, the particles may have geometric characteristics, (e.g. spokes or notches) that only allow the particles to deposit into the microwells in a particular orientation. The particle could also have geometric characteristics (e.g. protruding geometry or surfaces) that generate drag as the particles flow through a solution. The drag forces could cause the particles to flow into the microwells in a favored orientation.

Seed Cells and Detect

Figure 7A:
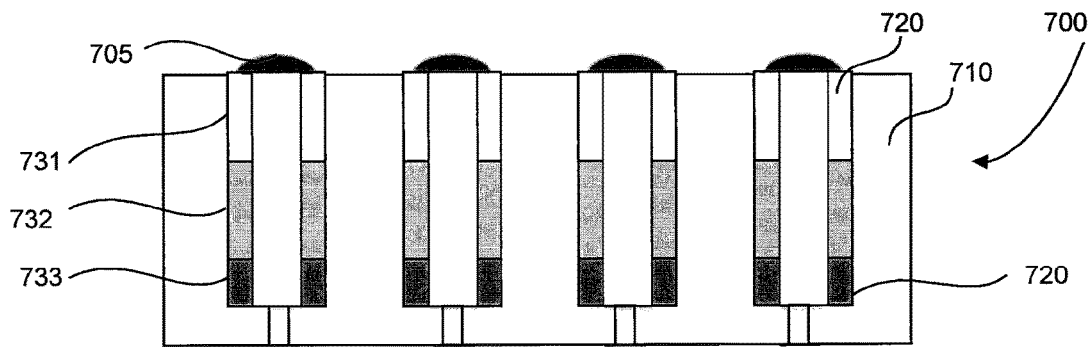
FIG. 7A is a side view of a particle sorting system with multifunctional particles loaded with cells.
Figure 7B:
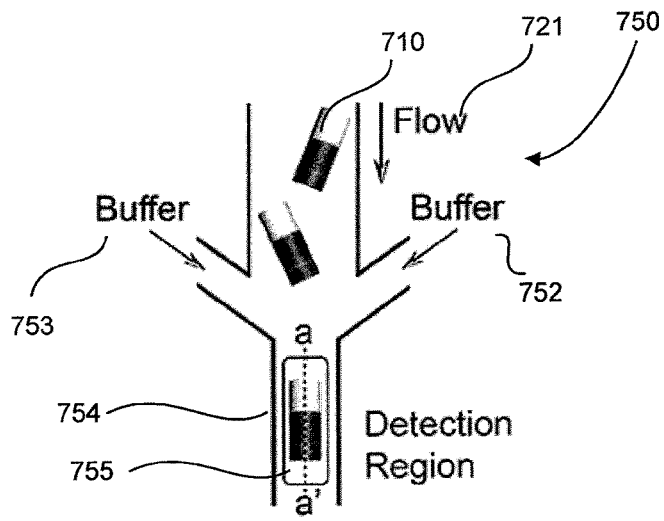
FIG. 7B is a schematic of a cell sorting system for sorting multifunctional particles with loaded cells.
Figure 7C:
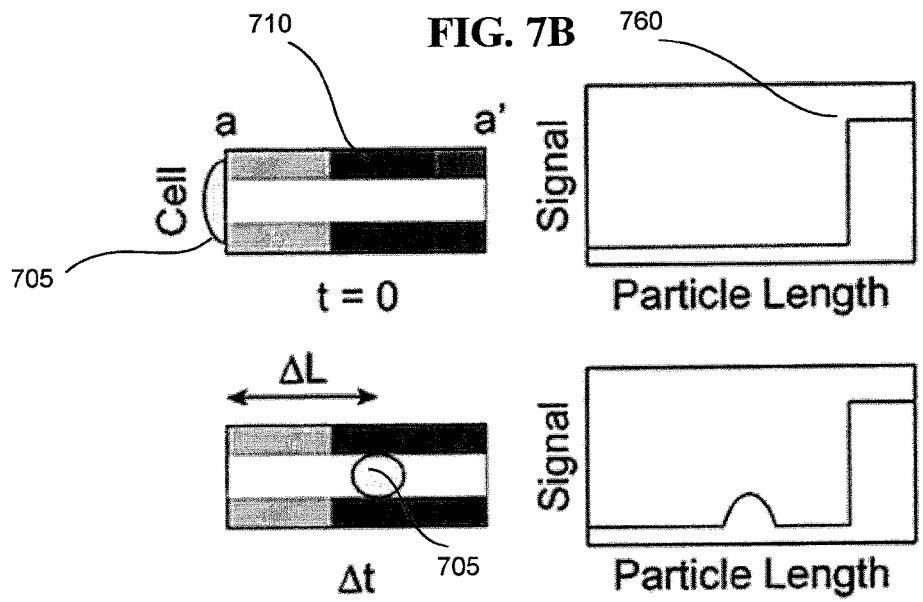
FIG. 7C is an example of signals that can be collected by the cell sorting device.

Referring to FIGS. 7A-C, the cell sorting system 700 provides a means to sort cells 705 based on cell motility. The cell sorting system 700 includes the particle orienting device 702—also described in detail above—so that cells 705 can deposit onto the top surface of the multifunctional particles 710. In the example as shown in FIG. 7A, the particle orienting device 702 is seeded with cells 705. In this example, the multifunctional particles 710 have three layers 731-733 of decreasing concentrations of biotinylated chemokines, which are bound to the surface of the multifunctional particles 710 via the streptavidin-biotin bond mentioned above. Layer 733 also includes magnetic nanoparticles so that, as described earlier, the multifunctional particles 710 have a uniform orientation within the microwells 720 of the particle sorting device 702. Each multifunctional particle can also include a marker, as described earlier, which can later serve as a geometric reference for measuring the distance a cell has traveled in a given period of time. Each multifunctional particle can have a tag, also described earlier, that serves as a unique identifier for a single microparticle. The multifunctional particles 710 are all oriented such that layer 731, which also favor cell adhesion due to incorporation of biotinylated collagen, sit at the entrance of the microwells 720 of the particle sorting device 702. A solution of cells 705 is poured onto the surface of the particle sorting device 702. Cells 705 are allowed to settle and eventually adhere to the top surface of the multifunctional particles 710.

As already mentioned, the number of layers and the combination and chemistry of extracellular matrix materials may vary depending on the implementation. In some embodiments, extracellular matrix materials on the top surface may include collagen to encourage cell adhesion. Also described earlier, the marker can be an optional feature. In some embodiments, the ends of the multifunctional particles can serve as a geometric reference surface for measuring cell motility. While the cells are described to settle onto the surface of the top surface of the multifunctional particles, a suction device operable with the particle orienting device could be used to induce a pressure differential such that the cells flow towards the top surface of the multifunctional particles.

After the cells 705 adhere to top layer 731, the multifunctional particles 710 are removed from the cell sorting system 700 with the cells 705 still captured by the multifunctional particles 710. The removal process can include reversing a flow of solution through the particle sorting device 702 such that the microparticles are released from the device 702 and re-suspended in solution. Now referring to FIG. 7B, a flow 721 of the multifunctional particles 710 are placed into a particle focusing device 750. Referring to FIG. 7C, chemotaxis causes the cells 705 to migrate along the gradient of chemokines formed on the multifunctional particles 710, going from low concentration of chemokines towards high concentration of chemokines. The chemotaxis may occur as soon as the cells are seeded on the multifunctional particles and can also occur upon releasing the microparticles from the particle orienting device 702. Referring back to FIG. 7B, the particle focusing device 750 can have continuous flows 752-753 of buffer solution that allow each multifunctional particle 710 to enter a detection region 755 to be interrogated using fluorescence microscopy techniques. As described above, flow-focusing techniques involving the flows 721 and 752-753 can be used to direct the multifunctional particles 710 through the detection channel 754.

The system 700 further includes an imaging system (not shown) configured to capture images and/or video of the cell 705 and multifunctional particle 710 as it passes through the detection region 755. For example, the imaging system is configured to perform time-lapse imaging, and can include a Zeiss Axiovert microscope operating at a 20X magnification. The system 700 also includes a computer system (not shown) that is operatively coupled to the imaging system, which captures an image of the microparticle in the detection region 755. The computer system can include a computer-readable storage medium (for example, a hard disk, a CD-ROM, and the like) that stores computer program instructions executable by data processing apparatus (for example, a computer system, a processor, and the like) to perform operations. The operations can include controlling the imaging system to capture images of the migration of cells 705 through the detection region 755. In addition, the computer system can receive the captured images from the imaging system, and process the images to obtain a migration speed of a cell 705 in a channel. The computer system can also execute a decision protocol after interrogating a microparticle to determine where to physically sort the microparticle.

Each multifunctional particle 710 can undergo several interrogation events. Referring to FIG. 7C, an interrogation event can be an image of the multifunctional particles 710 taken in the detection region 755 by the imaging system, and a sequence of interrogation events at specific times for a single multifunctional particle 710 can be post-processed to determine a strength of fluorescent signal 760 across the length of the multifunctional particle 710 over a particular time span Δt. The interrogation event can determine the orientation of the microparticle 710 based on the fluorescent signal 760 due to, due to, for example, references on the microparticle 710, such as a fluorescent, geometric marker or tag. The fluorescent signal can also identify the multifunctional particle 710 and determine the motility of the specific cell 705 captured in the specific multifunctional particle 710 by measuring a distance travelled ΔL over the time span Δt. For example, migration rates of the cells 705 can be tracked, and the migration rates can be calculated using Image J (NIH) software executed by the computer system. Further, the computer system is configured to execute computer software applications that perform statistical analysis of the data captured by the imaging system. For example, the computer system can be configured to execute the Shapiro-Wilk test to test the normality of the distribution of migration speed values for cells 705 in the same sample. The test indicates if the data is likely to be derived from a normally distributed population (p>0.05). The computer system is further configured to perform multivariate analysis to determine correlations between cell migration speed and clinical parameters. As a result, the phenotype for motility of the cell 705 can be determined from the images.

The computer system, after determining the phenotype of a cell 705, can decide where to physically sort the multifunctional particle 710 containing the cell. For example, if the cell 705 has a phenotype of interest, mechanical actuators that change the direction of flow after the detection channel 755 can be employed to direct the flow to a collection reservoir for cells with phenotypes of interest. In other implementations, magnetic fields, electrical fields, or other means of producing a force on the multifunctional particle or flow of multifunctional particles can be used to sort the microparticles.

Typical strategy for sorting requires the optical interrogation of the particles (detection region 115), a decision protocol for the processed information, and a downstream actuator to physically separate the particles. Optical interrogation may determine (1) the orientation of the particles (e.g. based on fluorescent markers at one end of the particles, combinations of fluorescent and geometry, and/or "barcoded" arrays of markers) and/or (2) A phenotypic parameter of the cell: e.g., the shape of the cell, the location of the cell on the particle (of the target phenotype is motility), the relative position of mitochondria with respect to the nucleus, among other phenotypes. For the separation of the particles, mechanical actuators that change the direction of flow streams, magnetic fields that are turned on and off, electrical fields, could be employed to separate the particles using current state of the art in microfluidics.

While the particle focusing device 700 is an exemplary device to determine the motility phenotype of the cell 705, it should be understood that alternative embodiments may examine other phenotypes, such as the shape of the cell or the relative position of mitochondria with respect to the nucleus. For example, the particle focusing device may be configured to measure an electrical, chemical, magnetic, or mechanical signal that may change depending on a phenotype of the cell. As described previously, reference markers are not limited to optical or fluorescent markers and may also include mechanical, magnetic, electrical, and other properties. While an imaging system is presented and described to visualize optical and fluorescent characteristics to detect the phenotypes and reference markers, other systems may include a magnetic imaging system, a conductivity sensing system, a tensile test machine, or other system to measure or detect a property of the multifunctional particles and cells of interest. Some of these examples will be described in more detail later. While the particle focusing device is shown in FIG. 7B to have a single detection region 755, any number of detection regions can be implemented for a given application. The number of conduits can also vary. The buffer solution can be modified so as to ensure the cells and multifunctional particles of an application do not interact with the buffer solution.

The multifunctional particles described herein can be used to analyze different types of motile cells. Some of the different types of cells, components of a chemokine solution in which each cell experiences a chemotaxis effect, cell sizes, and corresponding side channel sizes, are shown in Table 1.

TABLE 1

| Cell type | Chemoattractants |
|---|---|
| Neutrophils | IL8, fMLP, LTB4, C5a |
| T Lymphocytes | SDF1, CXCL10, CCL19, |
| Dendritic Cells | CCL19, CCL21 |
| Monocytes | MCP1, CCL7 |
| Eosinophils | eotaxin, RANTES, MCP-3, MCP-4, CCR3 |
| NK cells | MIP-1 alpha, MCP-1, RANTES, CXCL14 |
| B cells | SDF1, CCL11 |
| Lymphoblast | CCL22, MCP1 |
| Reticulocytes | SDF1 |
| Platelets | Collagen |
| Circulating Tumor Cells (CTCs) | SDF1 |
| Circulating Endothelial Cells (CECs) | VEGF, FGF, NO, S1P |

The cells herein can be isolated from blood samples using known techniques. For example, using sterile techniques, neutrophils can be isolated from whole blood by density gradient separation using Polymorphprep™ (13.8% sodium diatrizoate and 8.0% polysaccharide, Axis-Shield, Rodelokka, Oslo, Norway), with centrifugation at 500 g for 40 minutes. To return the cells to an isotonic environment, the cells can be harvested and re-suspended in 10 mL of 0.5× PBS, then isolated by centrifugation at 400 g for 10 minutes. The neutrophils can be re-suspended in 50-100 µL of 1× PBS before loading into the microfluidic device 100. Samples can be processed within one hour after each blood draw and can be maintained at 37° C.

Applications

Sorting Cancer Cells

During tumor cell invasion and metastases, small subpopulations of faster-moving cancer cells play a disproportionate role in accelerating the cancer dissemination processes. There is heterogeneity in the motility phenotype of clonal populations of cancer cells; more specifically, cancer cells having the same genetic material can move at different rates. Anterior localization of mitochondria is associated with faster migration velocities and increased directional persistence. Perturbing the asymmetric mitochondria localization by interfering with mitochondrial fusion (opa-1) and fission (drp-1) proteins reduces the number of cells with anterior localization of mitochondria and decreases the average migration velocity and the directional persistence of the fastest cells. Thus, order of magnitude differences in cancer cell migration may be predicted by the localization of mitochondria. It is possible then that if the mechanisms responsible for the asymmetrical distribution of mitochondria in moving cancer cells are identified, interventions could emerge increasing the time for cancer cells to travel between primary tumor and lymph nodes from months to years. These mechanisms are unlikely to be genetic, considering that the two daughter cells display distinct migration speed and persistence between them and with respect to the mother cell. These mechanisms are more likely the consequence of differences in phosphorylation levels of various proteins transporting mitochondria inside cells. To identify these mechanisms, sensitive proteomic analysis has to be performed. This analysis will require millions of cells in uniform populations having mitochondria at the front and corresponding controls having mitochondria at the back.

In some implementations, the techniques described herein can be used to separate cells based on mitochondria localization during migration. For example, tubular microparticles can enable the imaging of moving cells in response to EGF gradients inside the microparticles, detection of mitochondria asymmetry, and separation of cells with mitochondria in front of the nucleus. As described above, cells can deposit onto the surface of the tubular microparticles, and cell motility phenotype can be observed for the cells. The techniques described herein can sort a large number of cells by their cell motility phenotype and form uniform population of cells sharing similar mitochondrial localization characteristics. The uniform population of cells can then be used for proteomic analysis. Other emerging migration patterns, like the ability to orient through mazes, to squeeze through dense matrix, to secrete matrix-degrading enzymes, or migrate collectively could further enhance the relevance of separation phenotypes for cancer progression.

Sorting Neurons

Recent research in Alzheimer disease has uncovered that the uptake and propagation of misfolded tau proteins through entorhinal cortex layer II neurons could explain a decade old observation that the neuronal damage occurs in a hierarchical pattern, starting with the neurons connected to memory related neural systems. A critical question that arises from these observations is why some populations of neurons are protected while others develop tangles, in otherwise homogenous and anatomically connected neuronal populations. Investigation of this question may require the separation of at least two populations of neurons based on orthogonal properties of tau uptake and transport and neuronal excitability (including response to electrical and chemical stimuli).

The techniques disclosed herein may be used to separate and study live neurons without causing damage to the axons or inducing rapid stress responses. For example, neuronal axonal growth may be facilitated inside openings in the microparticles. Similar to the methods described above, neurons can be deposited onto the surface of microparticles in a known orientation. The microparticles can have characteristics that can be used to encourage axonal growth. For example, the microparticles may be fabricated with several conductive layers in the form of an electrical coil, similar to an inductor. A magnetic field can be applied so as to generate currents through the conductive layers of the microparticles, thus delivering electrical stimuli to neurons captured by the microparticles. While changing magnetic fields can induce electrical currents, performing this on thousands of neurons in a short time and separating the responding ones will be orders of magnitude more efficient than current clamping technique and compatible with the separation of responsive neurons.

Sorting Neutrophils

Chronic inflammation is a common pathology for seven out of ten top leading causes of mortality in the developed world (from atherosclerosis and heart disease to diabetes and cancer). Although therapeutic approaches targeting of chronic inflammation exist, by inhibiting the immune responses they also increase susceptibility to infections. can be effective on short term, diagnosis of chronic inflammation is often made when the damage to critical organs is already significant and irreversible. The ability to monitor chronic inflammation may enable early diagnosis, allow sufficient time to adopt lifestyle changes, assist early treatments, and may have major implications for reducing morbidity and mortality. In recent years, innate immunity in general and neutrophils in particular are emerging as unexpected and critical players in chronic inflammation. One particular phenotype, of neutrophils reversing their migration to return from sites of sterile inflammation into circulation has been proposed to be responsible for perpetuating inflammation throughout the body, leading to chronic inflammation. The reversely-migrating neutrophils can re-enter distant tissues, and through the production of cytokines like LTB4 stimulate more neutrophils to enter these tissues, increasing the chances for tissue damage. One hypothesis is that when the number of reversely-migrated neutrophils that are present in the blood passes a certain threshold, small inflammation processes in tissues can become self-sustained, leading to chronic inflammation.

The techniques disclosed herein for sorting cells may be used to investigate the foregoing hypothesis as well as study potential treatments. For example, neutrophils may be loaded onto microparticles with pockets and/or channels having smaller cross section than neutrophils, such that neutrophils can enter the channels only by active migration. The microparticles may also include chemokine concentration gradients that induce a motile response in some of the neutrophils. The microparticles then may be separated and analyzed based on one or more properties of the loaded neutrophils. The results of such studies and analysis may assist in developing novel capabilities for diagnostic and monitoring of chronic inflammation in patients.

EXAMPLES

The invention is further described in the following examples, which do not limit the scope of the invention described in the claims.

Example 1

Varying Concentration of Extracellular Matrix Materials on Particles

The purpose of this example was to show that anisotropic streptavidin-incorporated microparticles can be fabricated. The microparticles in this example were fabricated to have five distinct layers of varying concentrations of streptavidin. The protocol below describes (i) the fabrication of the anisotropic microparticles using stop-flow lithography and (ii) the incorporation of fluorescent markers to detect the concentration of streptavidin in each layer of the anisotropic microparticle.

Fabrication of Microparticles

The chemical composition of the microparticles is determined by the stop-flow lithography parameters and their geometry by the mask shape and channel height. A short UV exposure time of less than 0.2 s for was sufficient for the instant conjugation of streptavidin to PEG monomers during the microparticle polymerization process. Mixing streptavidin and N-hydroxysuccinimide (NHS)-PEG-acrylate introduced an acrylate functional group. The NHS group was covalently bonded with amines in streptavidin by the coupling reaction. The streptavidin-PEG-acrylate was mixed with PEG monomer solution, and this precursor solution was introduced into a PDMS microfluidic channel using a compressed air flow control system that generated pulsed operation of repeating "stop" and "flow" steps. During the "stop" step, a stationary array of microparticles are polymerized (with streptavidin incorporated into the microparticle network) via UV exposure. Microparticles are squares of 200-µm width and 60-µm height. Note that the short duration of UV exposure was sufficient to largely retain streptavidin activity. During the "flow" step, the polymerized microparticles were advected within the surrounding unpolymerized precursor solution and harvested in the collection reservoir.

Incorporation of Fluorescent Markers

Figure 8A:
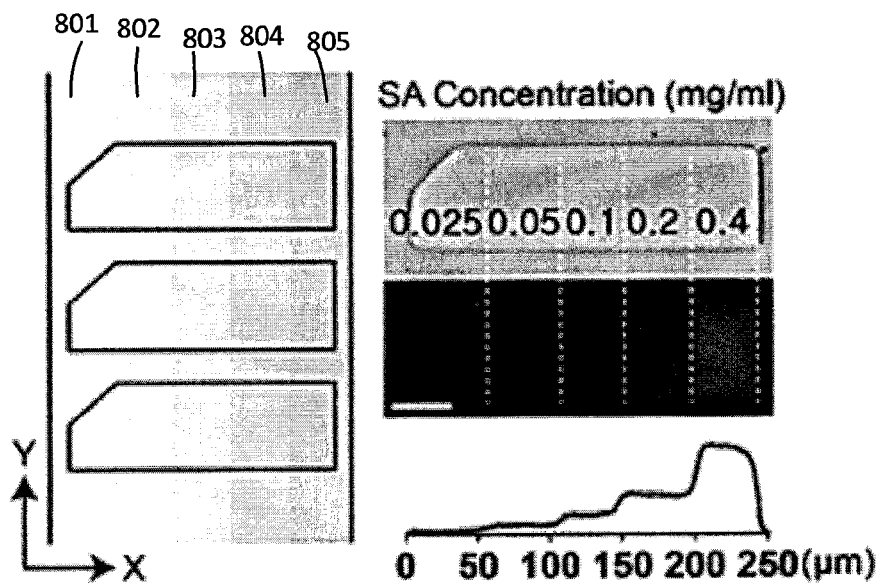
FIG. 8A is an example of multifunctional particles fabricated to have a varying concentrations of streptavidin.

To confirm incorporation of functional streptavidin into the microparticles, the polymerized microparticles with biotin-labeled fluorescein isothiocyanate (FITC) were incubated. The microparticles were rinsed to remove unbound biotin-FITC. The amount of streptavidin incorporated into the microparticles were adjusted by changing the concentration of the streptavidin-PEG-acrylate in precursor solutions. Precursor solutions containing five different concentrations of the streptavidin-PEG-acrylate were prepared (0.025 mg/ml, 0.05 mg/ml, 0.1 mg/ml, 0.2 mg/ml, and 0.4 mg/ml), and parallel flows of the precursor solutions were generated using a simple 2D flow-focusing technique. The channel Reynolds number in the working regime was $\sim 10^{-3}$, which was sufficiently low to create stable laminar flows. The monomer residence time prior to polymerization was ~0.6 (s), which was short enough to prevent diffusion between the interfaces of adjacent flow streams. Referring now to FIG. 8A, shape-coded microparticles consisting of five distinct regions 801-805 indicated by lowest streptavidin loading on one end region and highest streptavidin loading on the opposite end region were used to define microparticle orientation.

Results/Analysis

Figure 8B:
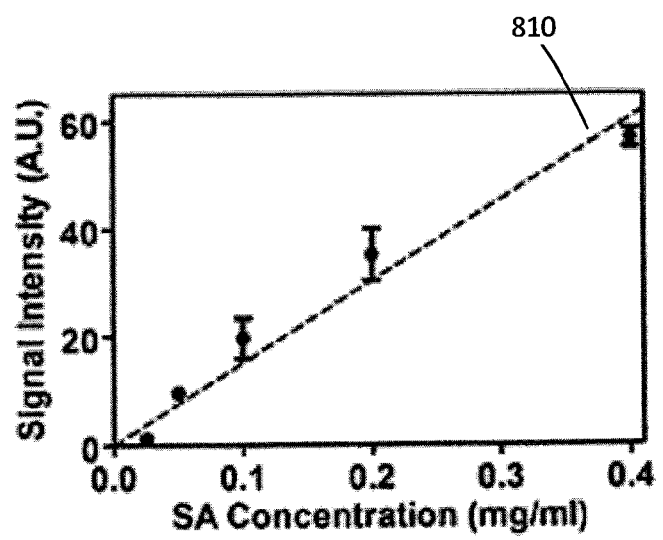
FIG. 8B is a plot of signal intensity versus streptavidin concentration.

Incubating the microparticle with biotin-FITC, the microparticles were scanned to detect the intensity of the fluorescent signal in each layer. The microparticles exhibited a stepwise increase in fluorescence signal intensity that corresponded to increased streptavidin concentration in a given region. The stepwise increase indicated limited diffusion between layers during the preparation of parallel laminar flows in fabricating the microparticles. Referring to FIG. 8B, a simple linear relation 810 between fluorescent signal intensity and streptavidin concentration was measured.

Example 2

Conjugation of Extracellular Matrix Materials

Similar experiments were performed to demonstrate the multifunctional particles can be fabricated to have different geometries that a variety of extracellular matrix materials can be bound to the streptavidin-incorporated anisotropic microparticles. The protocol below describes the conjugation procedure using collagen and poly-L-lysine.

Conjugating with Collagen

The microparticles were fabricated using the methods described in Example 1. Hexagonal and tubular geometries were created using stop-flow lithography. In this example, different ECMs were conjugated to the microparticles. Various ECMs were conjugated to the streptavidin-incorporated microparticles by biotinylating the ECMs. ECM materials have amine groups that can be functionalized using the NHS chemistry. Mixing ECMs and NHS-PEG-biotin generated biotinylated particles. The mixing ratio was determined by the stoichiometry between the mole numbers of amines in ECMs and NHS-PEG-biotin. In this example, collagen was used as a model ECM due to its vast abundance in nature. FITC-labeled collagen was used to evaluate collagen attachment to streptavidin-incorporated microparticles based on fluorescence signal intensity. Collagen and NHS-PEG-biotin were mixed at a mole ratio of 1:100. The streptavidin-incorporated microparticles were incubated with biotin-PEG-collagen.

Conjugating with Poly-L-lysine

Microparticles were also coated with poly-L-lysine. Poly-L-lysine is a commercially available synthetic polymer that is positively charged in water, and widely used for coating cell culture surfaces to improve cell-adhesion by altering surface charges. The number of amine groups in poly-L-lysine is a factor of 10 lower than what is found in collagen. As a result, biotinylated poly-L-lysine was mixed with NHS-PEG-biotin at a mole ratio of 1:10 poly-L-lysine. Streptavidin-incorporated tubular microparticles 915 were then incubated with biotinylated poly-L-lysine (which is also labeled with FITC).

Results/Analysis

Figure 9A:
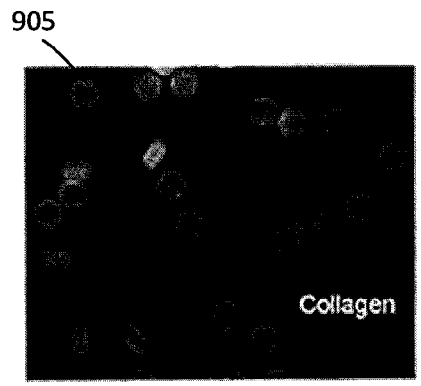
FIG. 9A is an example of fluorescein isothiocyanate (FITC)-labeled biotinylated collagen conjugated to the streptavidin in hexagonal multifunctional particles.
Figure 9B:
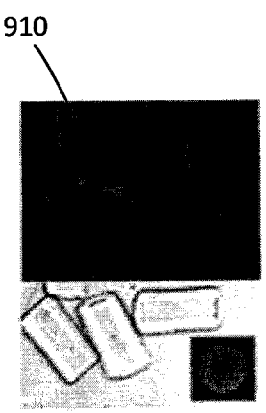
FIG. 9B is an example of FITC-labeled biotinylated collagen conjugated to the streptavidin in tubular multifunctional particles.
Figure 9C:
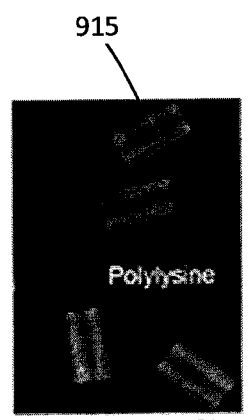
FIG. 9C is an example of FITC-labeled biotinylated poly-L-lysine conjugated to the streptavidin in tubular multifunctional particles.

Successful polymer attachment was detected based on fluorescence signal intensity. Referring to FIG. 9A, the hexagonal microparticles 905 were homogeneously conjugated with collagen via streptavidin-biotin click chemistry. The hexagonal shapes (among others) can be useful for close packing assembly. Collagen-conjugated anisotropic microparticles with various shapes can be prepared using this approach. For example, now referring to FIG. 9B collagen-conjugated tubular microparticles 910 with non-unity aspect ratio were fabricated. Due to its high aspect ratio, these microparticles easily toppled over. They can be used for the end-to-end assembly at fluid interfaces. Referring to FIG. 9C, poly-L-lysine can also be used as an ECM to bind to the streptavidin. These results suggest that stop flow lithography can be used as a general way to attach various ECMs to anisotropic microparticles based on streptavidin-biotin click chemistry.

Example 3

Janus Microparticles

Janus particles are particles with surfaces of two or more distinct functions or properties. In this example, spatial control of ECM coatings could be achieved by patterning streptavidin and rhodamine in PEG microparticles, thus forming Janus microparticles.

Fabrication of Particles

A stable two-phase flow was generated by infusing different precursor solutions into the two inlets of a PDMS microchannel. One stream is composed of PEGDA with streptavidin-PEG-acrylate, while the other stream consists of PEG-DA with a fluorescent dye (i.e., rhodamine acrylate). Janus triangular and square microparticles were synthesized at the interface between the two flows using the stop-flow lithography method described in this application and in Example 1.

Conjugating with Collagen

After the lithography step, the microparticles were incubated with the biotinylated collagen, similar to the process described in Example 2.

Results/Analysis

Figure 10:
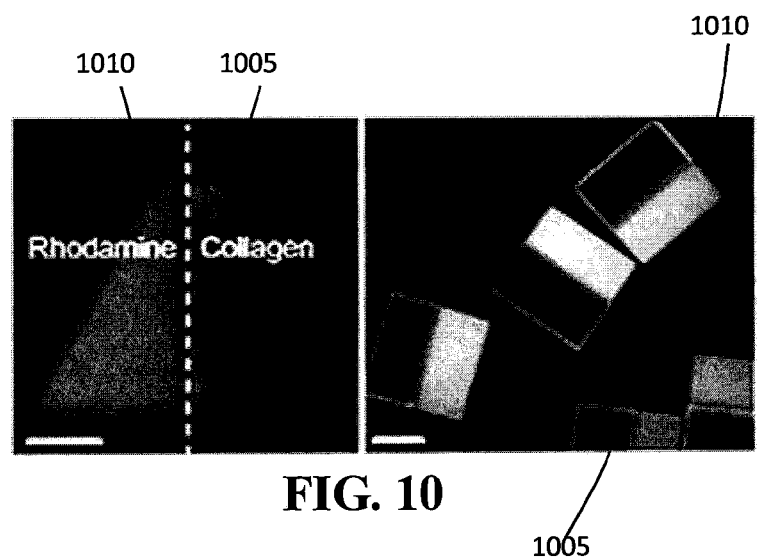
FIG. 10 is an example of a Janus particle composed of a first region having streptavidin bound to FITC-labeled biotinylated collagen and a second region having rhodamine.

Referring to FIG. 10, collagen was patterned only in a streptavidin region 1005 (shown in light grey) containing streptavidin. The streptavidin region 1005 fluoresced green due to the binding of collagen. The results indicate that streptavidin-biotin click chemistry and PEG anti-fouling properties can be used synergistically to pattern ECM materials onto polymerized structures with a high degree of spatial control. The rhodamine region 1010 (shown in dark grey) fluoresced red and therefore did not contain streptavidin. The ECM patterning process described here can be applied to more complex and multidimensional patterned microparticles synthesized from advanced flow lithography techniques such as lock release lithography, hydrodynamic focusing lithography, and oxygen-free flow lithography to produce microparticles with additional novel properties advantageous for self-assembly.

Example 4

Cell Adhesion and Phenotype Differentiation

The multifunctional particles can be configured to promote cell adhesion. In this example, the process of depositing monolayers of rat brain endothelial cells (RBE4) onto multifunctional particles is described.

Loading Brain Endothelial Cells

Figure 11A:
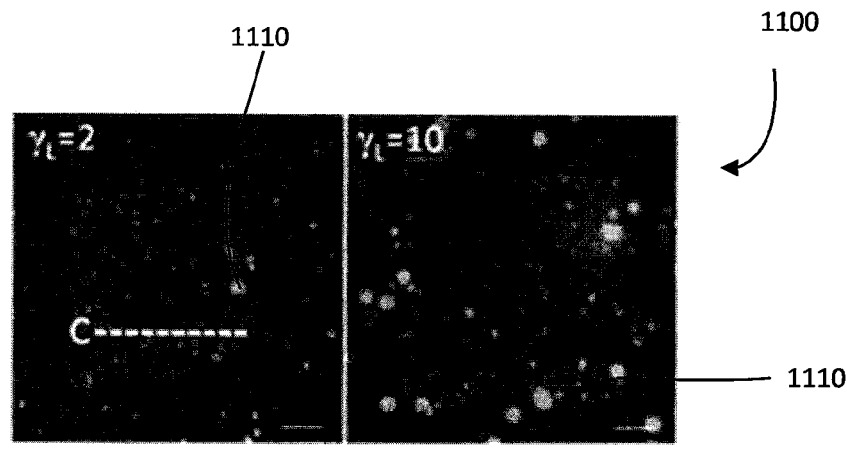
FIG. 11A is an example of rat brain endothelial cells loaded on the surface of multifunctional particles.

Referring to FIG. 11A, the size of the square microparticles 1100 (200 µm width and 60 µm height) was sufficient enough for the attachment of cells to top and side of the microparticles. Particles were fabricated using the stop-flow-lithography techniques described in Example 1. To facilitate the adhesion of the cells, collagen type I was used as the conjugated ECMs. Collagen type I has provided integrin-mediated cell adhesion, and been used for the RBE4 adhesion. The collagen-conjugated square microparticles were placed on a collagen-coated petri dish in a culturing medium. RBE4 was gently loaded onto the dish with the variation of a loading coverage, $\gamma L$. The dish was incubated overnight in a culturing incubator at 37° C. supplied with 5% CO2. The loading coverage was defined as the ratio of a total cellular area and the dish area. The number of the microparticles in each dish was around 20.

Results/Analysis

Figure 11B:
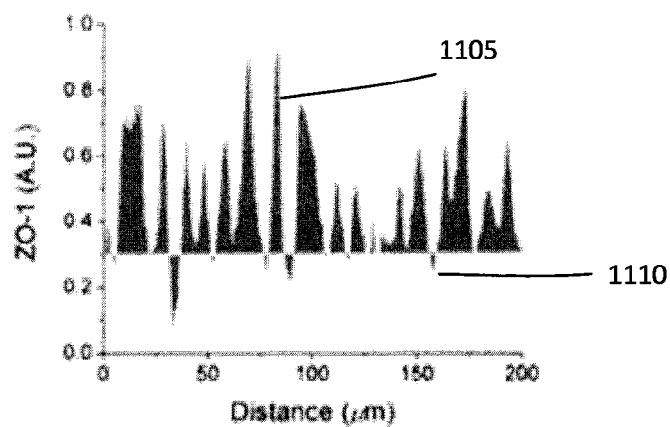
FIG. 11B is a plot of ZO-1 protein fluorescent signal from the culture of rat brain endothelial cells measured over a line C indicated in FIG. 11A.
Figure 11C:
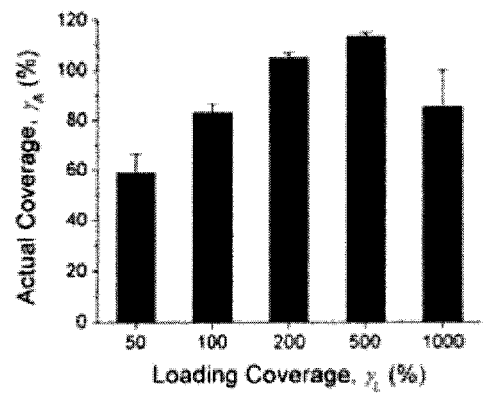
FIG. 11C is a graph of actual coverage based on the initial loading coverage of rat brain endothelial cells loaded in FIG. 11A.

The phenotype of the endothelial cells after adhesion to the microparticles was evaluated. The expression of ZO-1 protein was quantified, a marker for tight junctions between endothelial cells. The ZO-1 was significantly expressed along cellular boundaries, which represented strong tightness among cells. FIG. 11B shows a graphical representation of the expression of ZO-1 along a line in a multifunctional particle. Strong signals indicate a cellular boundary 1105, and weak signals indicate a nucleus 1110. The results show that a phenotype for strong tightness can be selected. Referring to FIG. 11C, the cell coverage of the microparticles, $\gamma A$, was defined as the ratio of an attached cellular area and a top area of microparticles. Loading coverage from 100 to 200% provided the actual coverage of 100% without causing multilayers of RBE4 nor detachment from the microparticles by overgrowth. This result shows the importance of the control over the cell loading coverage to achieve the 100% cell coverage on cell-laden microparticles.

OTHER IMPLEMENTATIONS

While this specification contains many specific implementation details, these should not be construed as limitations on the scope of any disclosures or of what may be claimed, but rather as descriptions of features specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. Thus, particular implementations of the subject matter have been described. Other implementations are within the scope of the following claims.

What is claimed is:

1. A method of sorting a plurality of cells, the method comprising:
   arranging a plurality of microparticles into an array on a substrate in a microfluidic device, wherein each microparticle of the plurality of microparticles comprises a plurality of reference markers embedded within the microparticle or attached to a surface of the microparticle
   wherein the plurality of reference markers are arranged in two or more regions, each region having a different overall concentration of the reference markers,
   wherein the plurality of reference markers comprise chemokines, and wherein the plurality of reference markers arranged in the two or more regions establish a chemokine concentration gradient within the microparticle or along the surface of the microparticle, and
   wherein the microparticle is tubular and has an opening that extends through the microparticle;
   introducing a plurality of cells to the array of microparticles under conditions that enable at least some of the cells to adhere to the microparticles;
   removing the plurality of microparticles, to which the cells are adhered, from the substrate;
   transferring the plurality of microparticles, to which the cells are adhered, to a detection region; and
   detecting, for each of two or more microparticles that pass through the detection region, a microparticle feature; and
   sorting the two or more microparticles based on the detected features, wherein the detected features are related to a phenotype of the cells.

2. The method of claim 1, wherein each microparticle of the plurality of microparticles comprises a porous material.

3. The method of claim 1, wherein the method further comprises allowing the cell that is adhered to the microparticle to propagate within or along the microparticle in response to the concentration gradient.

4. The method of claim 1, wherein each microparticle of the plurality of microparticles comprises a plurality of magnetic particles, and wherein arranging the plurality of microparticles comprises applying a magnetic field to the plurality of microparticles such that the microparticles align with the magnetic field on the substrate, and wherein removing the plurality of microparticles comprises removing the magnetic field.

5. The method of claim 1, wherein a surface of the substrate comprises a plurality of wells, wherein each well comprises a cross-section that matches a cross-section of one of the microparticles, and wherein arranging the plurality of microparticles comprises positioning the microparticles in the wells.

6. The method of claim 1, wherein introducing the plurality of cells to the array of microparticles comprises creating a pressure-differential that causes the plurality of cells to propagate in a direction of the array of microparticles, and wherein the substrate is porous, and wherein creating the pressure-differential comprises creating a fluid flow through porous regions of the substrate.

7. The method of claim 1, wherein detecting the microparticle feature comprises detecting a fluorescent signal from the microparticle, wherein the fluorescent signal corresponds to a position of a cell in or on the microparticle.

8. The method of claim 7, wherein, for each of the two or more microparticles, sorting is based on the position of the cell, and wherein the method further comprises determining, for at least one of the sorted microparticles, an amount that a cell has moved within or along the microparticle to which the cell is adhered.

9. The method of claim 1, further comprising, subsequent to introducing the plurality of cells, applying an electrical or chemical stimuli to two or more of the microparticles; and allowing cells to move or grow in response to the electrical or chemical stimuli, wherein the chemical stimuli is a chemokine concentration gradient, and wherein the plurality of reference markers comprises chemoattractants arranged to establish the chemokine concentration gradient.

10. The method of claim 1, wherein the plurality of cells comprises neurons, and wherein the method further comprises:
   subsequent to introducing the plurality of cells, applying an electrical stimulus to the neurons that are adhered to the microparticles;
   allowing axons to grow from the neurons in response to the electrical stimulus,
   wherein detecting the microparticle feature comprises detecting a fluorescent signal that corresponds to an extent of axon growth within or along the microparticle, and
   wherein the method further comprises sorting the two or more microparticles based on the how far each axon has grown.

11. The method of claim 1, wherein each microparticle of the plurality of microparticles further comprises a corresponding tag that uniquely identifies the microparticle.

12. The method of claim 11, wherein the tag is a bar-code.

13. A microparticle comprising:
   a plurality of reference markers embedded within the microparticle or attached to a surface of the microparticle,
   wherein the plurality of reference markers are arranged in two or more regions, each region having a different overall concentration of the reference markers,
   wherein the plurality of reference markers comprises chemokines, and wherein the plurality of reference markers arranged in the two or more regions establish a chemokine concentration gradient within the microparticle or along the surface of the microparticle, and
   wherein the microparticle is tubular and has an opening that extends through the microparticle.

14. The microparticle of claim 13, further comprising a tag that uniquely identifies the microparticle.

15. The microparticle of claim 14, wherein the tag comprises a bar-code.

16. The microparticle of claim 13, wherein the microparticle is porous, and wherein an average diameter of the pores in the microparticle ranges between about 10 nm to 100 nm.

17. The microparticle of claim 13, further comprising magnetic particles.

* * * * *

UNITED STATES PATENT AND TRADEMARK OFFICE
CERTIFICATE OF CORRECTION

PATENT NO. : 10,168,271 B2  
APPLICATION NO. : 15/033272  
DATED : January 1, 2019  
INVENTOR(S) : Daniel Irimia and Ki Wan Bong Page 1 of 1

It is certified that error appears in the above-identified patent and that said Letters Patent is hereby corrected as shown below:

In the Specification

Column 1, Lines 15, insert -- STATEMENT OF FEDERALLY SPONSORED RESEARCH
This invention was made with government support under Grant Nos. EB002503, and GM092804 awarded by the National Institutes of Health. The government has certain rights in the invention. --

Signed and Sealed this  
Twentieth Day of August, 2024

Katherine Kelly Vidal  
*Director of the United States Patent and Trademark Office*